(12) United States Patent
Lin

(10) Patent No.: US 9,669,166 B2
(45) Date of Patent: Jun. 6, 2017

(54) DISPOSABLE SYRINGE AND PUSH ROD FOR THE SAME

(71) Applicant: SOL-MILLENIUM MEDICAL HK LIMITED, Hong Kong (CN)

(72) Inventor: Zuoqian Lin, Zhejiang (CN)

(73) Assignee: SOL-MILLENNIUM MEDICAL HK LIMITED, Hong Kong (CN)

( * ) Notice: Subject to any disclaimer, the term of this patent is extended or adjusted under 35 U.S.C. 154(b) by 0 days.

(21) Appl. No.: 14/405,627

(22) PCT Filed: Dec. 28, 2012

(86) PCT No.: PCT/CN2012/087908
§ 371 (c)(1),
(2) Date: Dec. 4, 2014

(87) PCT Pub. No.: WO2013/181919
PCT Pub. Date: Dec. 12, 2013

(65) Prior Publication Data
US 2015/0148743 A1    May 28, 2015

(30) Foreign Application Priority Data

Jun. 6, 2012 (CN) .......................... 2012 1 0188526

(51) Int. Cl.
*A61M 5/315* (2006.01)
*A61M 5/42* (2006.01)
(Continued)

(52) U.S. Cl.
CPC .... *A61M 5/31515* (2013.01); *A61M 5/31501* (2013.01); *A61M 5/31511* (2013.01);
(Continued)

(58) Field of Classification Search
CPC ................ A61M 5/31515; A61M 5/50; A61M 5/31501; A61M 5/422; A61M 5/502;
(Continued)

(56) References Cited

U.S. PATENT DOCUMENTS 3,669,111 A    6/1972 Dubner
4,346,708 A *  8/1982 LeVeen ................. A61M 5/486
                                                    604/224
(Continued)

FOREIGN PATENT DOCUMENTS

CN    1152882 A    6/1997
CN    1961982 A    5/2007
(Continued)

OTHER PUBLICATIONS

Notification of Transmittal of the International Search Report and the Written Opinion of the International Searching Authority, or the Declaration dated Apr. 4, 2013 in corresponding International Application No. PCT/CN2012/087908, 14 pgs.
(Continued)

*Primary Examiner* — Manuel Mendez
(74) *Attorney, Agent, or Firm* — Shumaker & Sieffert, P.A.

(57) ABSTRACT

The present invention provides a disposable syringe and a push rod for use in a disposable syringe. The push rod comprises a proximal end, a distal end and an axis extending through the proximal end and the distal end. The distal end of the push rod is provided with a snap-fitting mechanism and a stop flange located at a proximal side of the snap-fitting mechanism. The stop flange comprises a main body portion formed about an axis of the push rod and a plurality of finger-like portions extending from the main body portion in a direction away from the axis of the push rod. According to the present invention, a smaller push force continues to be
(Continued)

applied to the push rod upon completion of the injection, thereby achieving an additional stroke needed when the distal end of the push rod snap-fits with the needle seat and meanwhile lessening the patient's pains.

9 Claims, 5 Drawing Sheets

(51) Int. Cl.
  *A61M 5/50* (2006.01)
  *A61M 5/31* (2006.01)
(52) U.S. Cl.
  CPC .............. *A61M 5/422* (2013.01); *A61M 5/50* (2013.01); *A61M 5/502* (2013.01); *A61M 5/504* (2013.01); *A61M 5/31513* (2013.01); *A61M 2005/3143* (2013.01); *A61M 2005/31508* (2013.01); *A61M 2005/31516* (2013.01)
(58) Field of Classification Search
  CPC .... A61M 5/31511; A61M 2005/31508; A61M 2005/3143; A61M 5/31513; A61M 2005/31516
  See application file for complete search history.

(56) References Cited

U.S. PATENT DOCUMENTS

| | | | | |
|---|---|---|---|---|
| 5,352,200 | A * | 10/1994 | Hammett | A61M 5/3216 604/110 |
| 2005/0080381 | A1* | 4/2005 | Hsieh | A61M 5/322 604/197 |
| 2005/0107747 | A1 | 5/2005 | Shih | |
| 2006/0178625 | A1 | 8/2006 | Lim | |
| 2007/0073223 | A1* | 3/2007 | Huang | A61M 5/31511 604/110 |
| 2010/0179487 | A1 | 7/2010 | Woehr | |

FOREIGN PATENT DOCUMENTS

| | | |
|---|---|---|
| CN | 101287514 A | 10/2008 |
| CN | 101743027 A | 6/2010 |
| CN | 101862490 A | 10/2010 |
| CN | 202569095 U | 12/2012 |
| EP | 2554204 A1 | 2/2013 |
| JP | 2006501944 A | 1/2006 |
| RU | 2065757 C1 | 8/1996 |
| WO | 9530444 A1 | 11/1995 |
| WO | 9906086 A1 | 2/1999 |
| WO | 2004033006 A2 | 4/2004 |
| WO | 2007019170 A1 | 2/2007 |
| WO | 2011160364 A | 12/2011 |
| WO | 2013153121 A2 | 10/2013 |

OTHER PUBLICATIONS

Extended Search Report from counterpart European Application No. 128785862, dated Jan. 25, 2016, 6 pp.

Search Report from counterpart Moroccan Application No. 37607, dated Aug. 22, 2016, 4 pp.

Office Action and Search Report, and translation thereof, from counterpart Russian Application No. 2014152481, dated Dec. 2, 2016, 11 pp.

Office Action and Search Report, in the Chinese language, mailed Jan. 24, 2017 in corresponding CN Application No. 201210188526.8, 8 pgs. (No Translation Available).

* cited by examiner

DISPOSABLE SYRINGE AND PUSH ROD FOR THE SAME

This application is a national stage entry under 35 U.S.C. §371 of International Application No. PCT/CN2012/087908, filed Dec. 28, 2012, which claims the benefit of CN Application 201210188526.8, filed Jun. 6, 2012. The entire contents of International Application No. PCT/CN2012/087908 and CN Application 201210188526.8 are incorporated herein by reference.

TECHNICAL FIELD

The present invention relates to a disposable syringe and a push rod for use in a disposable syringe.

BACKGROUND

In order to avoid cross infection caused by repeated use of the syringe, a disposable syringe is extensively used in medical practices. A typical disposable syringe comprises a barrel, a push rod reciprocatingly moveable in the barrel and a rubber piston in contact with the inner wall of the barrel. A distal end of the push rod and a needle seat mounted at a distal end of the barrel form snap-fitting mechanisms which can be engaged with each other. On the push rod is formed a stop flange located at a proximal side of the snap-fitting mechanism, and the rubber piston is mounted between the snap-fitting mechanism of the push rod and the stop flange. The stop flange is a boss-shaped structure and approximately rigid as compared with the rubber piston. During injection, the stop flange pushes and presses the rubber piston so that the rubber piston pushes a liquid medicament out of the syringe. When the rubber piston is pushed to a zero line, i.e., when the injection is finished, the rubber piston is braked. At this time, the push rod continues to be pushed and pressed, the stop flange will press the rubber piston into deformation so that the push rod can continue to advance distally such that the front end of the push rod is snap-fitted with the needle seat. Then, the push rod is pulled proximally, the needle seat is pulled in the barrel via the snap-fitting mechanism to complete self-destruction of the syringe and prevent the syringe from reuse.

However, in such disposable syringe in the prior art, in order to obtain an additional stroke whereby the distal end of the push rod continues to advance to engage with the needle seat upon completion of the injection, there is a need to apply a larger force to the push rod to cause the rubber piston to produce sufficient deformation. This causes the syringe strenuous in use and increases the patient's pains.

SUMMARY

In order to solve the above problems, according to an aspect of the present invention, there is provided a disposable syringe, comprising a barrel, a push rod and a rubber piston. The barrel comprises a proximal end, a distal end and a hollow interior. The hollow interior is defined by a barrel-shaped inner wall. The push rod is located and movable in the interior of the barrel. The push rod comprises a proximal end located outside the proximal end of the barrel, a distal end located in the interior of the barrel, and an axis extending through the proximal end and the distal end of the push rod. The distal end of the push rod is provided with a stop flange. The rubber piston is mounted on the push rod and located at the distal side of the stop flange and configured to come in contact with the inner wall of the barrel in a liquid tight manner. The stop flange comprises a main body portion formed about the axis of the push rod and a pushing and pressing portion extending from the main body portion in a direction away from the axis of the push rod and configured to push and press the rubber piston. The pushing and pressing portion is constructed in a way that when the rubber piston is stopped at the distal end of the barrel, only the pushing and pressing portion deforms as continuing to push and press the rubber piston.

According to another aspect of the present invention, there is provided a push rod for use in the disposable syringe, comprising a proximal end, a distal end and an axis extending through the proximal end and the distal end. The distal end of the push rod is provided with a stop flange. The stop flange comprises a main body portion formed about an axis of the push rod and a pushing and pressing portion extending from the main body portion in a direction away from the axis of the push rod.

According to the present invention, the stop flange comprises a main body portion in the middle and a pushing and pressing portion extending outward from the main body portion. The pushing and pressing portion forms a cantilever structure which is liable to deformation. Therefore, according to a conventional design, the rubber piston may be braked upon completion of the injection; when the pushing and pressing portion continues to push and press the rubber piston, only the pushing and pressing portion deforms, thereby achieving an additional stroke needed when the distal end of the push rod snap-fits with the needle seat and meanwhile lessening the patient's pains.

DETAILED DESCRIPTION

A disposable syringe and a push rod for use in the disposable syringe according to the present invention will be described with reference to the specific embodiments shown in the figures. Those skilled in the art should appreciate that what is shown in the figures is only exemplary and intended to illustrate the present invention, not to limit the present invention.

The directional terms "distal" and "proximal" used in the following detailed description are relative to medical care personnel such as a nurse for injecting for a patient, and respectively correspond to "up" and "down" of the page of FIGS. 1-3.

Figure 1:
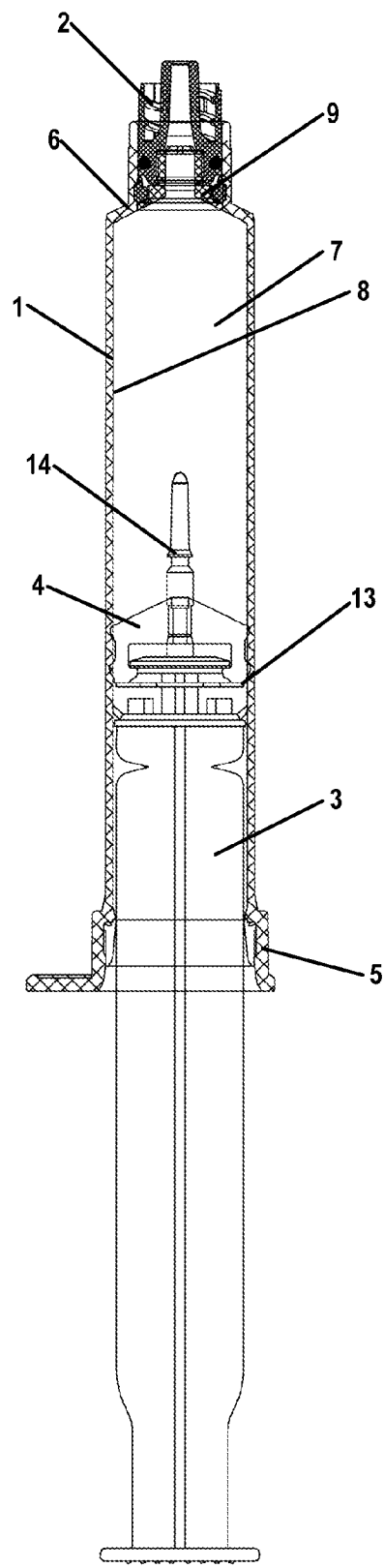
FIG. 1 is a cross-sectional view of a disposable syringe according to one embodiment of the present invention, wherein the syringe is in an in-injection state.
Figure 2:
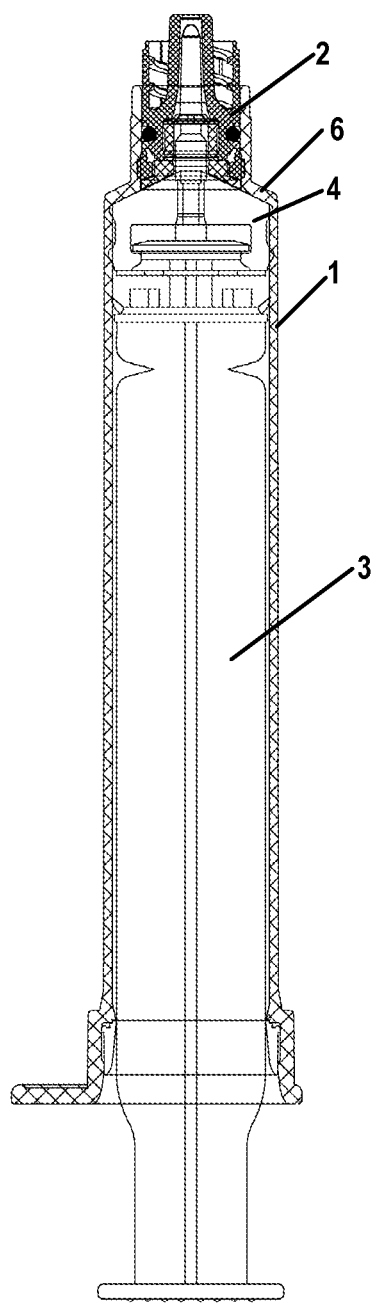
FIG. 2 illustrates a state of the syringe of FIG. 1 upon completion of the injection.
Figure 3:
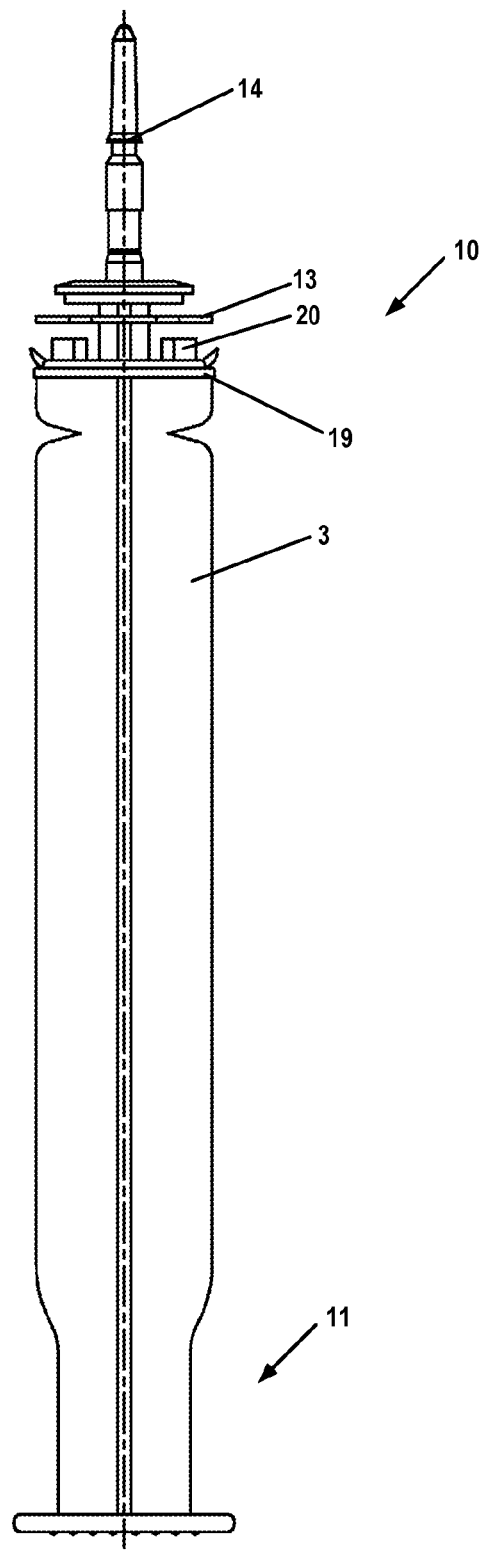
FIG. 3 is an elevation view of a push rod for use in a disposable syringe according to an embodiment of the present invention.

FIG. 1 and FIG. 2 respectively illustrate a disposable syringe according to one embodiment of the present invention in two states, namely, an in-injection state and a state upon completion of injection. As shown in the figures, the disposable syringe of the present invention comprises a barrel 1, a needle seat 2, a push rod 3 and a rubber piston 4. The barrel 1 comprises a proximal end 5, a distal end 6 and a hollow interior 7. The hollow interior 7 is defined by a barrel-shaped inner wall 8. The rubber piston 4 is mounted on the push rod 3 and comes in contact with the inner wall 8 to achieve liquid sealing and the discharge of a liquid medicine needed by the injection. The needle seat 2 is located at the distal end of the barrel 1 and comprises a snap-fitting mechanism (a first snap-fitting mechanism) 9.

The push rod 3 is mounted in the interior 7 of the barrel 1 and movable in the interior of the barrel 1. Meanwhile, referring to FIG. 3, the push rod 3 comprises a distal end 10 located in the interior 7 of the barrel, a proximal end 11 located outside the proximal end 5 of the barrel, and an axis 12 extending through the proximal end 11 and the distal end 10 of the push rod. The distal end 10 of the push rod is provided with a stop flange 13 and a snap-fitting mechanism (a second snap-fitting mechanism) 14 located at the distal side of the stop flange 13. The second snap-fitting mechanism 14 is adapted to engage with the first snap-fitting mechanism 9 upon completion of the injection so that when the push rod 3 is pulled proximally, the needle seat 2 snap-fitted with the push rod 3 can be pulled into the interior 7 of the barrel 1, thereby achieving self-destruction of the disposable syringe. The snap-fitting mechanisms 9 and 14 of the needle seat and of the push rod may be any suitable mechanism known in the art and used for self-destruction of the syringe after use. The present invention does not relate to improvements to the snap-fitting mechanism itself, so the detailed structure of the snap-fitting mechanism will not be descried herein any more.

Referring to FIG. 1 and FIG. 2, more specifically, the rubber piston 4 is mounted at the distal end 10 of the push rod 3 and located between the second snap-fitting mechanism 14 of the push rod 3 and the stop flange 13. When the push rod 3 moves distally, the stop flange 13 pushes and presses the rubber piston 4 so that the rubber piston 4 moves distally along with it to discharge the liquid medicament out of the interior 7 of the barrel 1 through a needle on the needle seat 2; after the rubber piston 4 is braked upon completion of the injection, the stop flange 13 continues to push and press the rubber piston 4 to produce an additional stroke needed by the push rod 3 to engage with the needle seat 2.

Figure 4:
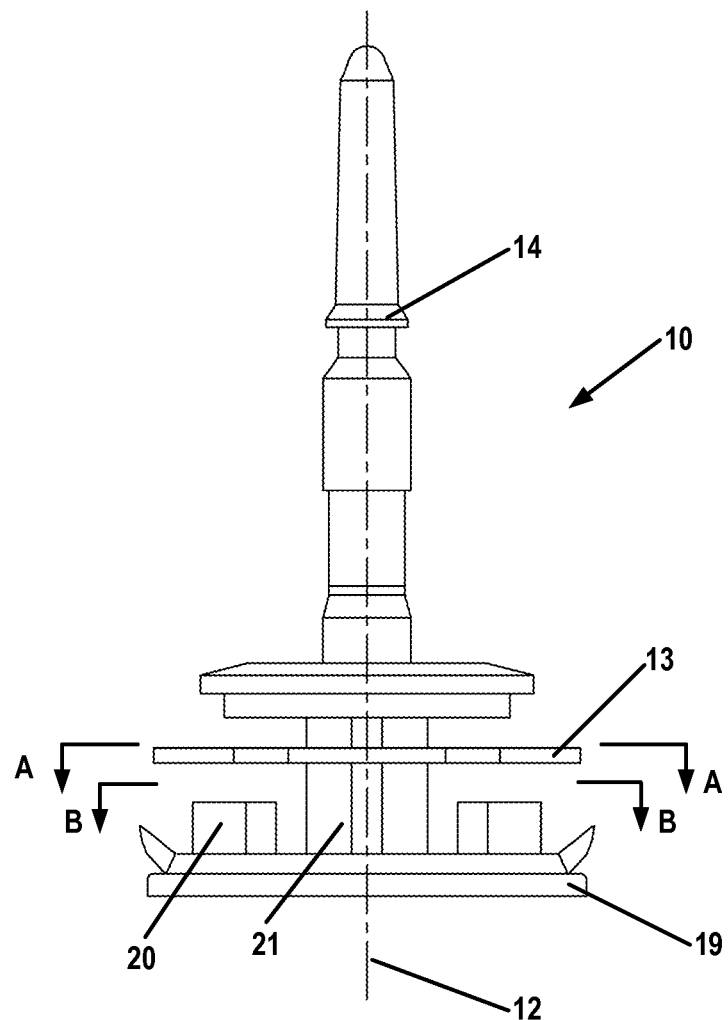
FIG. 4 is an enlarged view of a distal portion of the push rod of FIG. 3.
Figure 5:
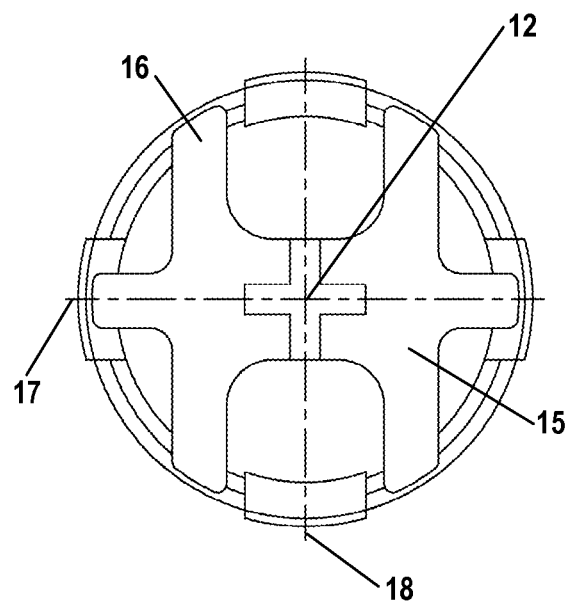
FIG. 5 is a cross-sectional view taken along line A-A of FIG. 4.
Figure 6:
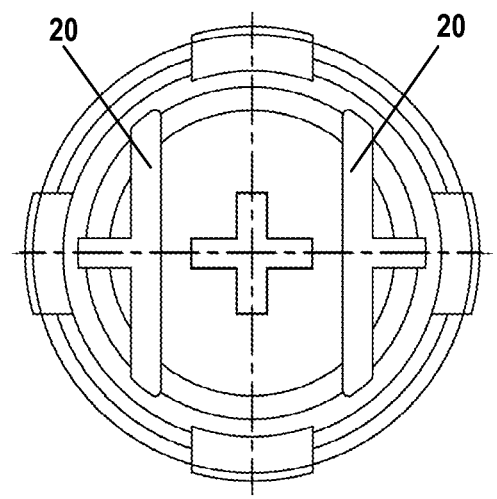
FIG. 6 is a cross-sectional view taken along line B-B of FIG. 4.

Referring to FIG. 4, FIG. 5 and FIG. 6, in the push rod 3 for use in the disposable syringe according to the present invention, the stop flange 13 is preferably made of an elastic material. The stop flange 13 comprises a main body portion 15 formed about the axis 12 of the push rod 3 and a pushing and pressing portion 16 extending from the main body portion 15 in a direction away from the axis 12 of the push rod 3. Therefore, the pushing and pressing portion 16 extending out of the main body portion 15 forms a cantilever structure. In the disposable syringe according to the present invention, the pushing and pressing portion 16 of the cantilever structure is used to push and press the rubber piston 4.

In specific embodiment shown in the figure, the pushing and pressing portion 16 is comprised of a plurality of finger-like portions. Those skilled in the art can readily envisage that the pushing and pressing portion 16 has a predetermined rigidity by virtue of customary designs such as selection of a material, a selection of the shape and a selection of the cross-section shape. During the injection, the sum of a frictional force and a liquid medicament resistance between the rubber piston 4 and the inner wall 8 of the barrel 1 is very small. Therefore, when the pushing and pressing portion 16 pushes the rubber piston 4 to move distally, the pushing and pressing portion 16 itself deforms very little or substantially does not deform. Upon completion of the injection, the rubber piston 4 is stopped at the distal end 6 (namely, a zero line) of the barrel 1, and an acting force and a counterforce produced by the pushing and pressing portion 16 continuing to push and press the rubber piston 4 will increase, whereupon only the pushing and pressing portion 16 deforms under the counterforce of the rubber piston 4, i.e., only the pushing and pressing portion 16 deforms and the rubber piston 4 does not deform. The deformation of the pushing and pressing portion 16 provides an additional stroke which is needed when the distal end 10 of the push rod 3 continues to move distally and enables the second snap-fitting mechanism 14 of the push rod 3 to engage with the first snap-fitting mechanism 9 of the needle seat 2. As compared with the rubber piston 4, the pushing and pressing portion 16 is more likely to deform. Therefore, as compared with the situation in the prior art in which a larger force is needed to deform the rubber piston 4, in the present invention only a smaller force is needed to finish the additional stroke needed by the push rod 3 for engagement of the snap-fitting mechanisms and to reduce the patient's pains. In the embodiment shown in FIG. 5 and FIG. 6, the plurality of finger-like portions of the pushing and pressing portion 16 are symmetrically distributed relative to a plane through the axis 12 such as planes 17 and 18, namely, arranged symmetrically relative to the plane. It is appreciated that the plurality of finger-like portions may be distributed symmetrically about the axis 12, namely, arranged symmetrically about the axis. The main body portion 15 in the figure is generally rectangular, four finger-like portions on the upper side and the lower side have the same shape, and two finger-like portions on the left side and the right side have the same shape. However, the finger-like portions on the upper and lower sides and the finger-like portions on the left and right sides are different in length and width. It can be appreciated that the main body portion 15 may be in any shape. The plurality of finger-like portions may be the same or different; they may be distributed symmetrically or asymmetrically. In the embodiment shown in FIG. 4, the stop flange 13 is wholly in a shape of a sheet generally perpendicular to the axis, or at least the plurality of finger-like portions therein are in the shape of sheets generally perpendicular to the axis.

It should be appreciated that the pushing and pressing portion 16 may be in any other shape besides the finger shape, for example, a circular shape or a polygonal shape, so long as it can meet the desired deformation.

In order to limit the deformation degree of the pushing and pressing portion 16, or in order to prevent too much deformation of the pushing and pressing portion 16, a limiting boss 20 may be disposed at a proximal side of the stop flange 13 of the push rod 3. In a specific example shown in FIGS. 3 and 4, at the distal end of the push rod 3, a platform (e.g., a circular boss) 19 with ratchets is formed at the proximal side of the stop flange 13. The limiting boss 20 is a boss formed on the platform 19 and having a shape corresponding to the finger-like portion 16.

In a push rod of a further preferred embodiment not shown, a portion of the push rod 3 closely adjacent to the proximal side of the stop flange 13 is a bendable portion. In the present invention, "closely adjacent" means that there not other structures between two portions. Referring to FIG. 3 and FIG. 4, in a specific embodiment, the bendable portion 21 is located between the stop flange 13 and the circular boss 19. The bendable portion 21 is formed to have a smaller diameter or thickness than other portions of the push rod 3, or formed by any structure which is known by those skilled in the art and can produce a bent deformation.

In the case that the whole push rod is rigid, upon injection, if a push force is not coincident with the axis of the push rod, the push rod might deflect to bring the rubber piston to deflect so that a water tight function between the rubber piston and the inner wall of the barrel loses, which causes leakage. When the push rod is assembled in the interior of the barrel, if the axis of the push rod deflects relative to the axis of the barrel, it might be difficult to mount the rubber piston in the barrel. The existence of the bendable portion can solve the above problem, and thereby facilitates use and assembling of the syringe.

Embodiments of the present invention are described in detail with reference to the drawings. Those skilled in the art should appreciate that the drawings and the corresponding depictions are only intended to illustrate the present invention. On this basis, those skilled in the art may make other variations and improvements which fall within the protection scope of the present invention.

What is claimed is:

1. A disposable syringe, comprising:
    a barrel, comprising a proximal end, a distal end and a hollow interior, the hollow interior being defined by a barrel-shaped inner wall;
    a push rod located in the interior of the barrel and movable in the barrel, the push rod comprising a proximal end located outside the proximal end of the barrel, a distal end located in the interior of the barrel, and an axis extending through the proximal end and the distal end of the push rod, the distal end of the push rod being provided with a stop flange; and
    a rubber piston mounted on the push rod and located at a distal side of the stop flange and configured to come in contact with the inner wall of the barrel in a liquid tight manner,
    wherein the stop flange comprises:
        a main body portion formed about the axis of the push rod, and
        a pushing and pressing portion configured to push and press the rubber piston and extending from the main body portion in a direction away from the axis of the push rod,
    wherein the pushing and pressing portion is constructed so that when the rubber piston is stopped at the distal end of the barrel, only the pushing and pressing portion deforms as continuing to push and press the rubber piston; and
    a needle seat located at the distal end of the barrel and comprising a first snap-fitting mechanism; the distal end of the push rod is provided with a second snap-fitting mechanism located at the distal side of the rubber piston, the second snap-fitting mechanism is adapted to engage with the first snap-fitting mechanism via deformation of the pushing and pressing portion upon completion of the injection.

2. The disposable syringe according to claim 1, wherein the stop flange is made of an elastic material.

3. The disposable syringe according to claim 1, wherein the pushing and pressing portion is in a shape of a sheet perpendicular to the axis.

4. The disposable syringe according to claim 1, wherein the pushing and pressing portion is comprised of a plurality of finger-like portions which are symmetrically distributed relative to a plane through the axis.

5. The disposable syringe according to claim 1, wherein the pushing and pressing portion is comprised of a plurality of finger-like portions which are symmetrically distributed about the axis.

6. The disposable syringe according to claim 1, wherein the push rod comprises a bendable portion closely adjacent to the proximal side of the stop flange.

7. The disposable syringe according to claim 1, wherein the push rod further comprises a limiting boss located at a proximal side of the stop flange to limit an amount of deformation of the pushing and pressing portion.

8. The disposable syringe according to claim 7, wherein the push rod further comprises a platform located at the proximal side of the stop flange, and the limiting boss is a boss formed on the platform and having a shape corresponding to the finger-like portion.

9. The disposable syringe according to claim 8, wherein a portion of the push rod between the platform and the stop flange is a bendable portion.

* * * * *